United States Patent [19]

Wagner

[11] E Patent Number: Re. 32,961

[45] Reissued Date of Patent: Jun. 20, 1989

[54] DEVICE FOR MEASURING LOCAL RADIATION ABSORPTION IN A BODY

[75] Inventor: Wolfgang Wagner, Norderstedt, Fed. Rep. of Germany

[73] Assignee: U.S. Philips Corporation, New York, N.Y.

[21] Appl. No.: 875,432

[22] Filed: Feb. 6, 1978

Related U.S. Patent Documents

Reissue of:

[64] Patent No.: 4,057,725
Issued: Nov. 8, 1977
Appl. No.: 610,616
Filed: Sep. 5, 1975

[30] Foreign Application Priority Data

Sep. 6, 1974 [DE] Fed. Rep. of Germany ..... 2442809

[51] Int. Cl.[4] ..... G01N 23/00

[52] U.S. Cl. ..... 378/4; 378/9; 378/10

[58] Field of Search ..... 250/445 T; 378/4, 9, 378/10, 15

[56] References Cited

U.S. PATENT DOCUMENTS 3,866,047 2/1975 Hounsfield ..... 378/4
3,881,110 4/1975 Hounsfield ..... 378/4

*Primary Examiner*—Craig E. Church
*Attorney, Agent, or Firm*—Jack E. Haken

[57] ABSTRACT

A device for measuring the spatial distribution of radiation absorption in a body wherein a multiplicity of radiators are regularly distributed about a circle surrounding the body, each radiator emitting a wedge-shaped beam of radiation in the plane of the circle toward a different arc portion of the circle beween two other radiators, a multiplicity of adjoining detectors in each arc portion measuring radiation from the radiator emitting radiation to that arc portion, the spatial distribution of radiation absorption being calculated from the measured radiation values of all the detectors.

9 Claims, 1 Drawing Sheet

DEVICE FOR MEASURING LOCAL RADIATION ABSORPTION IN A BODY

Matter enclosed in heavy brackets [ ] appears in the original patent but forms no part of this reissue specification; matter printed in italics indicates the additions made by reissue.

The invention relates to a device for measuring the spatial distribution of radiation absorption in a body, wherein the radiation to be emitted by at least one radiator is measured in a large number of directions by means of a number of detectors which are successively arranged in one plane in the body, each detector having only a comparatively small effective measuring field, the spatial distribution being calculated from these measuring values.

A device of this kind is known, for example from German Offenlegungsschrift 1,941,433. Therein, the radiator/detector system is displaced perpendicular to the radiation direction, and the absorption is measured in a large number of directly adjacent points. Subsequently, the radiator/detector system is rotated through a given angle, after which the operation is repeated, etc. The time required for obtaining the necessary measuring values in this apparatus amounts to a few minutes, so that using this apparatus only bodies or body parts can be examined which can be kept completely immobile, as otherwise disturbances occur due to lack of focus.

It is already known to reduce this measuring time (German Offenlegungsschrift 1,941,433, FIG. 7) by measuring the radiation emitted by the radiator by means of a plurality of detectors which are arranged in a arc of a circle around the radiator, each detector measuring the radiation stopped by a collimator associated with the detector. In order to measure the absorption in the parts which are not irradiated during a first measuring series, the detectors and the associated collimators are translated until all regions of the body to be examined and which have not yet been irradiated have been covered. Subsequently, the radiator and the associated collimators and detectors are rotated through a given angle, and simultaneously the detectors are translated back, after which the operation is repeated. The complete measurement, however, is still comparatively time-consuming in this apparatus. Moreover, always only a very small part of the radiation emitted by the radiator is used for the measurement (i.e. the radiation which is stopped by the collimators), so that when use is made of an X-ray tube as the radiator, this X-ray tube must be operated to the limit of loadability. This has an adverse effect on the service life of the X-ray tube and on the reliability of the apparatus.

The invention has for its object to provide a device for measuring the spatial distribution of the absorption of radiation in a body whereby the measuring time is reduced and in which the power of the radiator is more efficiently used.

To this end, a device of the kind set forth according to the invention is characterized in that the detectors are arranged in a row such that their effective measuring fields directly adjoin each other and cover the entire, approximately wedge-shaped stopped radiation of the radiator.

The invention will be described in detail hereinafter with reference to the drawing.

Figure 1:
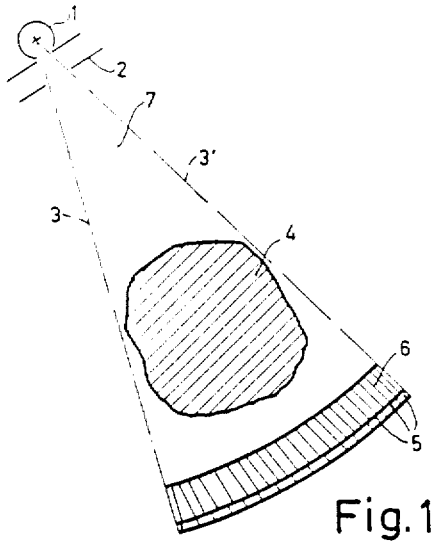
FIG. 1 is a diagrammatic view of a device according to the invention.

FIG. 1 shows a radiator 1 which can contain an X-ray tube or radio-active isotope. A collimator 2 passes a wedge-like beam 7 of emitted radiation, the outer limits of said beam being denoted by 3 and 3'. The beam 7 irradiates a body 4 to be examined. Behind the body 4, a large number of detectors 5 are arranged in a circle around the radiator 1 such that their effective measuring fields adjoin each other in a contacting manner, with the result that the overall radiation wedge 3,3' is measured by the individual detectors. Using this device, the absorption in the directions determined by the connecting lines between the radiator and the detectors 5 can all be measured in one operation. So as to obtain the absorption distribution in the other directions, the radiator/detector system is preferably continuously rotated about the body 4, the radiation source being switched on and the absorption being measured in given angular positions. Because the absorption in the plane of examination can be determined by way of a single measurement in one position of the radiator/detector system, a substantial reduction of the examination time (to a few seconds) is feasible.

A scattered radiation diaphragm 6 which is arranged in front of the detectors 5 and a collimator (not shown in the drawing) which limits the beam in the direction perpendicular to the plane of the drawing such that only the detectors are struck by the radiation, ensure that the scattered radiation density in the region of the detectors remains substantially smaller than in the case of conventional tomography. The scattered radiation density can be further reduced by arranging the detectors not directly behind the body, but rather at a larger distance therefrom, so that the opening angle as regards the scattered radiation centres in the body is reduced. In that case the geometrical lack of focus is increased, but this effect can be neglected, because in the device according to the invention—like in the known devices—substantially reduced spatial resolution is used. In particularly critical cases, the scattered radiation can be reduced by means of an additional diaphragm device to be provided between the collimator 2 and the radiator 1, if the said diaphragm opening is proportioned such that each time only a beam corresponding to the effective measuring field of one or only a few detectors is stopped, the diaphragm device being rotatable about the radiator such that during one rotation all detectors 5 are successively irradiated. The required time is thus increased, but the measuring time can still be reduced, because in such a device the moving mass is essentially smaller that in the known devices.

The detectors 5 may comprise radiation-sensitive PbO-crystallites or $HgI_2$-crystals, or use can alternatively be made of radiation-sensitive semiconductor detectors. For example, the use of light-sensitive photocells or photodetectors (photo-diodes, photo-field effecttransistors, etc.) is possible, these devices being preceded by an amplifier foil for converting X-radiation into visible light. The detectors can be operated such that they supply a signal which is proportional to the dose power (in this case pre-amplifiers which form the time integral of the output signal of the detectors must be connected behind the detectors) or they may be connected such that their output signal is proportional to the dose, so that the subsequent pre-amplifiers only have to amplify the signal. Because the measuring values of all detectors are each time simultaneously released for one direction, the subsequent computer (not elaborated herein) for measuring the spatial distribution of the absorption in the plane usually cannot process the measuring values in parallel; the detector output signals must therefor be applied to a storage element, for example, to a sample-and-hold amplifier, the outputs of all sample-and-hold amplifiers being connected to the computer via a multiplex device which successively applies the stored measuring values to the computer.

In addition to the row of detectors shown in FIG. 1, a further row of detectors may be provided in a direction perpendicular to the plane of the drawing, immediately adjoining the row of detectors shown. In that case, the radiation of the radiator must obviously be limited such that the two detector rows are struck by the radiation. During the subsequent processing of the measuring values supplied by the two rows of detectors, either the absorption distribution in the two planes determined by the detector rows can be measured or, after addition of the measuring values each time supplied by two adjacent detectors, the mean absorption distribution for the two planes can be calculated, the signal-to-noise ratio thus being improved.

In practice the fact must be taken into account that the intensity of the radiation emitted by the radiator is not uniformly distributed over the radiation wedge 3 and that the sensitivity of the individual cells may differ. To this end, the gain of the pre-amplifiers connected behind the detectors is adjusted such that, in the case of direct radiation by the radiator (i.e. without the body 4 being in the beam path) the output signals are preferably the same.

In order to prevent the distribution of the absorption in the plane of the body to be calculated from the measuring values from being influenced by temporary fluctuations in the radiation intensity, an additional detector can be provided which is arranged above or below the plane of the drawing, so that the radiation measured thereby on the one hand is not attenuated by the body 4, to be examined, and the detector on the other hand does not influence the radiation measured by the other detectors. To this end, the collimator arranged in front of the radiator must be provided with an additional opening in the correct position. The absolute values of the measuring values, being dependent of temporary fluctuations in the intensity of the radiator, should then no longer be used for the calculation, but rather the ratio between the measuring values of the row of detectors 5 on the one side and that of the additional detector on the other side, this ratio being independent of such fluctuations.

For the operation of the device it is important that the row of detectors is directed exactly to the radiation beam formed by the collimators in front of the radiator. Alignment can be effected by means of an optical adjusting device (not shown) which is permanently connected to the radiator 1 and which emits light rays by means of a mirror device, the position and the direction of the two outer light rays corresponding to the position and the direction of the boundary lines 3,3', whilst the third light ray coincides with the bisector between these two rays. The row of detectors 5 can thus be more readily directed to the radiator. Moreover, the light rays produce light spots on the object to be examined, the layer to be measured thus being optically marked.

Figure 2:
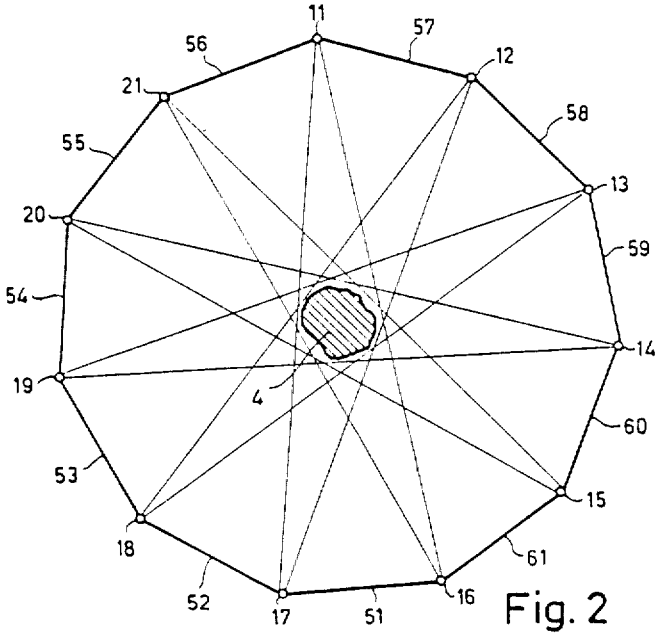
FIG. 2 shows such a device comprising various radiators arranged in a circle.

FIG. 2 shows an embodiment of the device according to the invention which enables a further reduction of the measuring time. Therein, a number of radiators (11 in the drawing) 11–21 are arranged in a circle, in the centre of which the object 4 is to be arranged, each time a row of detectors 51–61 being associated with the said radiators, diametrically opposite in the space between two adjacent radiators. Using this device, the absorption in the plane of the body can be simultaneously or almost simultaneously measured in a number of directions corresponding to the number of radiators.

If all radiators were simultaneously switched on, the scattered radiation density would be substantially increased in comparison with the device shown in FIG. 1. So as to avoid this phenomenon, the X-radiators and the associated rows of detectors can be successively switched on. This can be effected within fractions of seconds.

On the basis of spatial and economic considerations, in practice the number of radiator/detector systems cannot be made as high as the number of directions in which the absorption is to be measured in the separate regions of the plane of the body to be examined. In order to measure the absorption in all necessary directions, therefore, the system consisting of the radiators and the associated rows of detectors is rotated about the body to be examined (or the body relative to the system), during one rotation through the angle $2\pi/n$ ($n$=number of radiators) all radiators being actuated $m$ times, so that the absorption can be measured in $m \times n$ different directions. These measurements can be performed in a comparatively short time, because the device need be rotated only through a small angle and because the rotary movement can be continuously performed. Therefore, planes of bodies which can only be very briefly immobilized can also be examined.

What is claimed is:

1. A device for measuring the spatial distribution of radiation absorption in a body, comprising:

a multiplicity of radiators regularly distributed about a circle of diameter sufficient to surround said body, each radiator emitting a wedge-shaped beam of radiation in the plane of said circle toward a different arc portion of said circle between two other radiators; and a multiplicity of adjoining detectors in each of said different arc portions of said circle to measure radiation from the associated radiator emitting radiation thereto, each detector having only a comparatively small effective measuring field, the spatial distribution being calculated from the measured radiation values from said detectors.

2. The device defined in claim 1 wherein said circle of radiators and detectors is rotatable in the plane thereof with respect to said body to measure radiation values in different rotary orientations thereof.

3. The device defined in claim 2 wherein said radiators and detectors may be successively rendered effective.

*4. An apparatus for examining a body by means of penetrating radiation including a source means arranged to irradate the body with a planar spread of said radiation, detector means arranged to detect the radiation to provide output signals, relating to absorption of the radiation by the body, for processing to provide a representation of the distribution of absorption in a substantially planar section of the body and means adapted to scan the planar spread of radiation in relation to the body so as to irradate said section along a plurality of beam paths passing through the body from a plurality of direction, wherein said detector*

*means comprises a plurality of detector devices of which a predetermined number are irradiated by said spread at any time and wherein the scanning means is arranged to traverse the spread of X-rays along the detector device so as to change the irradiated device progressively.*

*5. An apparatus according to claim 4 wherein the scanning means include means adapted to move said source means in relation to the body to provide at least part of the scanning of said spread of radiation.*

*6. An apparatus according to claim 4 including means adapted to move said detector means relative to the body.*

*7. An apparatus according to claim 4 in which the scanning means include means adapted to provide at least a rotational motion of said spread of radiation relative to the body.*

*8. An apparatus according to claim 4 including collimator means adapted to restrict the number of said detector devices irradiated at any time.*

*9. An apparatus according to claim 8 including means for moving the collimator means in relation to the detector means to change the detector devices so irradiated.*

* * * * *